United States Patent [19]
Alving et al.

[11] Patent Number: 6,149,606
[45] Date of Patent: Nov. 21, 2000

[54] METHOD AND DEVICE FOR USE IN THE DIAGNOSIS OF INFLAMMATORY STATES IN THE UROGENITAL TRACT

[75] Inventors: Kjell Alving, Uppsala; Jan M. Lundberg, Djursholm; Jon Lundberg; Eddie Weitzberg, both of Stockholm; Peter Wiklund, Lidingö, all of Sweden

[73] Assignee: Aerocrine AB, Sweden

[21] Appl. No.: 09/156,000

[22] PCT Filed: Apr. 11, 1997

[86] PCT No.: PCT/SE97/00610

§ 371 Date: Dec. 8, 1998

§ 102(e) Date: Dec. 8, 1998

[87] PCT Pub. No.: WO97/37587

PCT Pub. Date: Oct. 16, 1997

[30] Foreign Application Priority Data

Apr. 11, 1996 [SE] Sweden .................................. 9601369

[51] Int. Cl.[7] .......................................................... A61B 5/00
[52] U.S. Cl. ............................................................ 600/562
[58] Field of Search .................................... 600/560, 587, 600/562; 604/26, 35, 36

[56] References Cited

FOREIGN PATENT DOCUMENTS

| | | |
|---|---|---|
| 9404161 | 11/1994 | Sweden . |
| 9502442 | 7/1995 | Sweden . |
| WO 9001893A1 | 3/1990 | WIPO . |

OTHER PUBLICATIONS

Alving, K., et al., "Increased amount of nitric oxide in exhaled air of asthmatics"; Dialog Information Service; File 154; (1994) Dialog Access. No. 07832223.

Lundberg, J.O.N., et al., "Primarily nasal origin of exhaled nitric oxide and absence in Kartagener's syndrome"; *Eur. Resp. J.*, 7 (1994) 1501–04.

*Primary Examiner*—Max Hindenburg
*Attorney, Agent, or Firm*—Banner & Witcoff, Ltd.

[57] ABSTRACT

Device and method for collecting endogenous gaseous nitric oxide (NO), in the urogenital tract, for example in the urinary tract and in the uterus and oviducts. According to one embodiment, a NO permeable, liquid impermeable inflatable body (16) is positioned in the urethra (5) surrounded by the prostate gland (17), whereby an additional inflatable body (4) positioned in the bladder (2) serves to seal off the bladder from the urethra and helps in the positioning of the device. The present invention further relates to a method and a system for use in the diagnosis of inflammatory states in said organs.

17 Claims, 5 Drawing Sheets

METHOD AND DEVICE FOR USE IN THE DIAGNOSIS OF INFLAMMATORY STATES IN THE UROGENITAL TRACT

FIELD OF THE INVENTION

The present invention relates to a novel method in the diagnosis of inflammatory states in inner organs, such as the urogenital organs, for example the urinary tract, uterus and oviducts. The present invention further relates to a new device and method for collecting endogenous gaseous nitric oxide (NO), in inner organs, such as the urogenital organs, for example the urinary tract, uterus and oviducts.

DESCRIPTION OF THE BACKGROUND OF THE INVENTION

Inflammatory conditions of the urogenital organs, for example in the urinary bladder (cystitis) and in the urethra (urethritis) often give rise to subjective symptoms, such as general discomfort, but also clinical symptoms, including urgency, dysuria, stricture and enuresis. In many cases the underlying causes are difficult to diagnose objectively. Patients with urgency symptoms from the lower urinary tract are very common. These symptoms may be due to inflammatory diseases or non-inflammatory functional disorders, and bladder biopsies are often required to distinguish between the two groups of patients. Inflammatory conditions in the uterus and oviducts are likewise often difficult to diagnose. A distinction between salpingitis and appendicitis may sometimes be practically impossible without preforming a diagnostic laparotomy. It is also of great importance to be able to rule out the occurrence of bacterial or viral infections, tumours or other pathological conditions, which untreated could have very severe consequences. Traditionally the investigation of previously mentioned symptoms has been performed through chemical and microbiological analyses of urine and discharge from said areas, ocular inspection e.g. urethroscopy and laparoscopy, the previous two often together with biopsy, followed by cultivation and/or studying the sample under microscope. Characteristic for many of said methods is, that they are time consuming, often require hospitalization and cause considerable discomfort to the patient.

STATE OF THE ART

It is previously known that NO is excreted into the airway lumen and is increased in exhaled air of asthmatic patients (Alving, K. et al., *Eur Resp J.* 6 (1993) 1386–70). Nevertheless large concentrations of NO are normally present in the nasal airways, without being a positive indication of any abnormal state (Lundberg, J. O. N. et al., *Eur Resp J*, 7 (1994) 1501–04). The role and occurrence of NO in the human body is still not conclusively investigated and many theories, often more or less incompatible, are presented. Further, greatly increased concentrations of NO have been measured in luminal gas sampled from the colons in patients with active ulcerative colitis (Lundberg, J. O. N. et al., *Lancet,* 344 (1994) 1673–4). NO has been found to be a clinically relevant marker for inflammatory conditions in the intestines and a patent application (SE 9404161-3) concerning a method for diagnosing such conditions, based on this finding is currently pending. Another related patent application, filed by the present inventors, concerns the collection of endogenous NO in the upper airways of tracheostomized or intubated patients and re-administration of the same gas in the inhaled airflow provided by the ventilator (SE 9502442-8). Said application is currently pending.

Tonometry, i.e. the measurement of the pressure inside a organ, has also been adapted to the sampling of gases in the gastrointestinal tract. Using a commercially available apparatus known as a Tonomitor®, $CO_2$ can be sampled in the gastrointestinal tract. The Tonomitor® consists of a silicone balloon, permeable to gases but not to liquids, attached to a sampling tube. The device is inserted in the lumen of the gut and the balloon is filled with saline. Over time the $pCO_2$ of saline infused into the balloon equilibrates with the $pCO_2$ of fluid in its proximity. The $pCO_2$ in the lumen equilibrates with the $pCO_2$ in the superficial layers of the mucosa with which it is in contact. The $pCO_2$ of saline aspirated from a Tonomitor® provides, therefore, an indirect measure of the $pCO_2$ in the superficial layer of the mucosa adjacent to the balloon of the Tonomitor®.

The closest prior art, known to the present inventors, is WO 90/01893, which discloses a remote sensing tonometric catheter apparatus and method. Although the description contains mentions of sensing and/or sampling a fluid or gas property, the only examples given are pH, $pO_2$ and $pCO_2$. Further, the description WO 90/01893 is occupied with the problem of early detection of intestinal ischemia. The description nevertheless mentions the use of a tonometric device in conjunction or combination with urinary catheters and ureteric catheters, yet no commercially available tonometer is physically suitable for insertion in the urinary tract. Symptomatically, the illustrations attached to WO 90/01893 show only the device inserted per naso in the stomach and per rectum in the gut. In the preferred embodiments, the membrane enclosed volume is expanded by filling it with an liquid, e.g. bicarbonate solution or saline. It can be summarized, that WO 90/01893 is concerned with indications (perfusion and ischemia), applications (gastrointestinal) and methods (analyzing pH, $pO_2$ and $pCO_2$ in liquid medium) greatly differing from and not anticipating the present invention.

DESCRIPTION OF THE INVENTION

The present invention relates to a device for localized collection of endogenous gaseous nitric oxide in the urogenital organs, for example the urinary tract, the uterus and oviducts according to attached claims 1 to 7. Said device consists of means for injecting and aspiring a gas of known composition in a cavity to be investigated. Preferably said device includes at least one inflatable body completely or partially made of NO-permeable and liquid impermeable material, a tube or tubes for inflation and sampling and means for inflating said body or bodies with a non reactive gas or gas mixture of known composition and aspiring and analysing the gas mixture aspired. The present invention also comprises a method, according to attached claims 8 to 15, for collection of endogenous gaseous nitric oxide, produced in the urogenital organs, for example the urinary tract epithelium, uterine or oviduct epithelium, characterized in that the endogenous gaseous nitric oxide is collected locally, from a defined inner cavity or a defined area on the epithelium on the inner or outer surface of an organ. The invention further comprises a method for detection and monitoring of local inflammatory states in the urogenital organs, for example in the urinary tract, the uterus and oviducts, characterized in that local production of gaseous nitric oxide is detected and quantified. The obtained level of NO is then compared to the level for healthy individuals or with a level obtained at another occasion for the same individual. An increased NO level is taken as an indication of an inflammatory state in the area or cavity investigated and can be used as an indication of, for example, any one of the following conditions; salpingitis, inflammation of the uterus, endometritis, endometriosis, prostatitis, extrauterine pregnancy, irradiation cystitis, chemically induced cystitis, interstitial cystitis and urethritis of different genesis.

The present inventors have now shown, that NO excretion from the surface epithelium in the urinary tract reliably correlates with inflammatory conditions, hitherto diagnosable only through urethroscopy or biopsy. According to the present invention, the detection of NO can be used for quantification of inflammatory conditions otherwise difficult to determine. Preliminary studies also indicate, that the same correlation exists for inflammatory conditions in the uterus and oviducts.

The recent finding by the present inventors, that increased levels of NO can be detected in normally not gas filled body cavities, such as the urogenital organs, for example in the urinary tract and in the uterus and oviducts, is unexpected and very surprising, specially in view of the above cited prior art. Traditionally the occurrence of nitrite in urine, i.e. elevated urinary levels of nitrite, has been attributed to bacterial conversion of nitrate to nitrite. The method of analysing urinary nitrite is not totally reliable, occasionally giving false negative results and consistently failing to detect sterile inflammatory states. It should also be noted, that nitrite containing urine normally does not release gaseous NO.

Contrary to the airway lumen, which is constantly filled with gas, and the intestinal lumen regularly containing gas pockets and bubbles, more or less evenly dispersed in the stomach and intestinal contents, the urogenital organs, for example the urinary bladder and the urinary tract, are normally void of gases. The same is true for the uterus and oviducts. The same NO flushing functions as encountered in the airways can therefore not be expected there.

Additionally the epithelium of the urinary tract differs from membranes encountered elsewhere in the body. The uroepithelium is generally recognised as highly impervious and therefore the excretion of NO must be considered surprising. Contrary to the epithelium in the airways and the intestines which obviously has evolved to allow efficient resorption of gases and nutrients, the urinary epithelium is required to be highly impervious and to function as a resorption barrier. Consequently the epithelial cells of the urinary tract differ in type from the ciliated epithelium of the airways and also from the columnar and cuboidal epithelium of the intestines.

The endogenous synthesis of NO has been studied, resulting in the division of NO-producing enzymes in $Ca^{++}$ dependent and $Ca^{++}$ independent enzymes. The general opinion is, that the $Ca^{++}$ dependent enzyme only has the ability to produce minute amounts of NO compared to the high producing, $Ca^{++}$ independent enzyme. The finding, by the present inventors, that the enzyme encountered in the urogenital organs is of the $Ca^{++}$ dependant type and has the ability to produce considerable amounts of NO is therefore highly surprising.

The invention will be described more thoroughly in the following, with reference to enclosed drawings and description of preferred embodiments.

DESCRIPTION OF THE PREFERRED EMBODIMENTS

The method according to the present invention can, in its most uncomplicated embodiment, be practised without the use of any special device, other than a catheter and a syringe for injecting a gas of known composition in an inner cavity or organ and aspirating a gas sample from said cavity or organ. Preferably, and according to the main features of the present invention, a device is used, which allows samples to be taken locally, in precisely defined locations in an organ or on the surface of any organ. More specifically the device according to the present invention is a device for localized collection of endogenous gaseous nitric oxide, characterized in that said device includes an inflatable body, made completely or partially of NO-permeable and liquid impermeable material, a tube for inflation and sampling and means for inflating said body with a non reactive gas or gas mixture of known composition and aspiring said gas or gas mixture and means for analysing the gas mixture aspired. Said means for inflation and aspiration can comprise e.g. a conventional syringe, fluid tightly connectable to said tube for inflation and sampling.

Said membrane can consist, completely or partially, of a NO-permeable and liquid impermeable material, for example chloroprene rubber, silicone or a suitable cation exchange membrane, such as Naphion® (E.I. du Pont de Nemours & Co).

A practitioner familiar in the field can easily select suitable materials for the inflatable body and other parts of the device. The present invention encompasses all improvements and modifications, obvious to someone skilled in the art. Naturally all materials used should be readily sterilizable, hypo-allergenic, non-reactive and generally suitable for endogenous use.

According to one preferred embodiment said device is adapted for use in connection with an urethroscope, vaginoscope, hysteroscope or similar instrument, which enables the exact positioning of said inflatable body for local sampling.

According to a further embodiment of the invention, said inflatable body of NO-permeable material has an anatomically suitable three-dimensional shape, adapted to specific organs and defined areas in specific organs. Said inflatable body of NO-permeable material can have any shape, suitable for investigations in or on the organ of interest, e.g. any one of the following shapes; cylindrical with rounded end surfaces, spherical, semi-spherical, conical, ellipsoid, pear-shaped or a flattened sphere or flattened ellipsoid.

Figure 1:
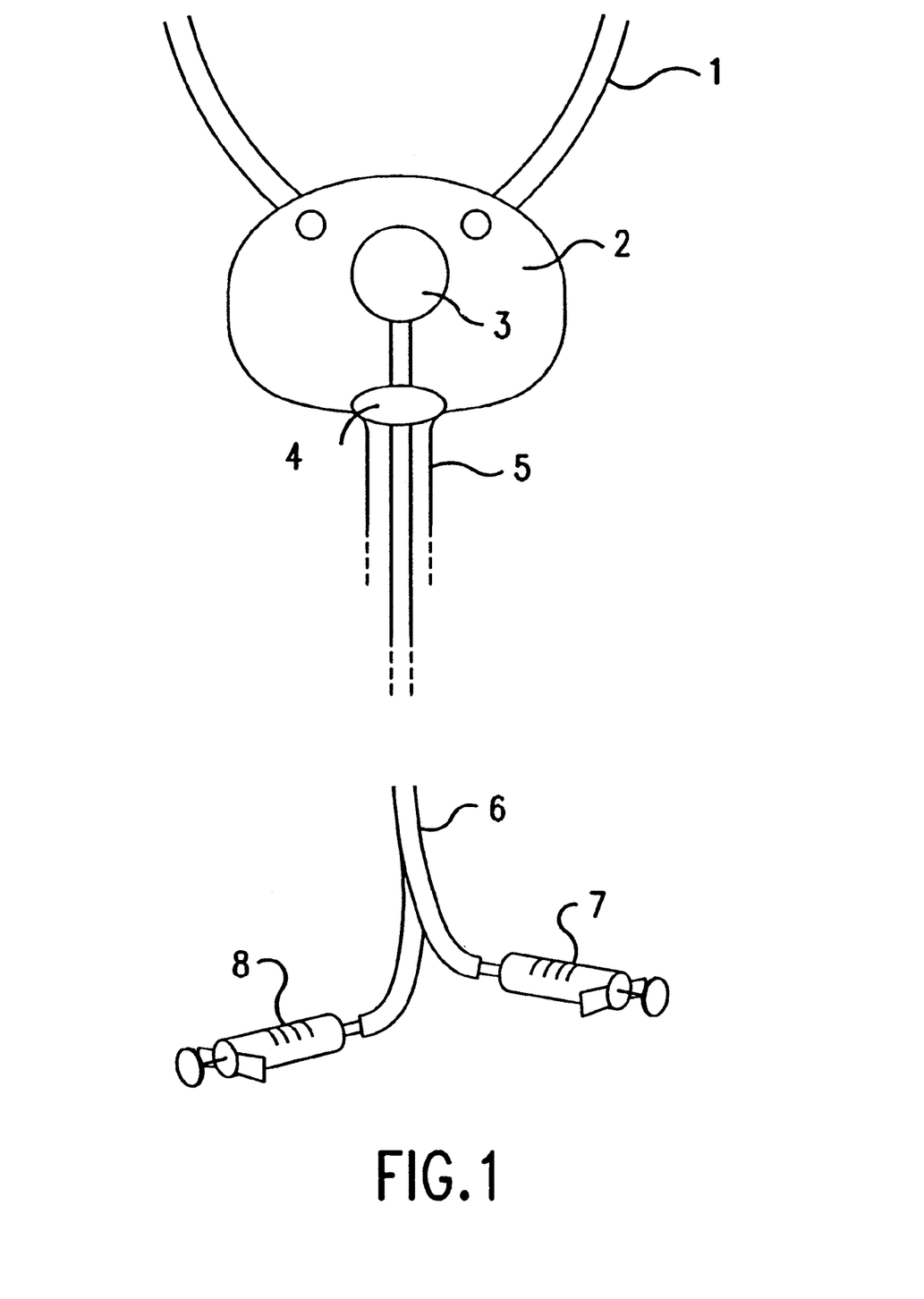
FIG. 1 shows an embodiment of the present invention where an inflatable body (3) been introduced in the urinary bladder, with an inflatable cuff (4) sealing the entrance to the urethra (5)

According to a further embodiment of the invention the device can include at least one inflatable body for positioning and/or anchoring the device during collection of the gas sample. Such additional body or bodies can function to seal off neighbouring cavities, for example separating the bladder and the urethra during sampling. This embodiment is exemplified in FIG. 1, which depicts the ureters (1), the bladder (2), an inflatable, NO permeable body (3), an additional inflatable body (4) for anchoring the device and sealing ol the bladder from the urethra (5), a catheter (6) and two devices, e.g. syringes (7 and 8) allowing for inflation of the inflatable bodies and, naturally, aspiration of a gas sample from the inflatable, NO permeable body (3). Note that the bladder (2) is depicted only schematically, whereas it in a patient would be collapsed or distended in a degree depending of it's content of urine. Using the inventive device in combination with a normal urinary catheter, this condition can easily be regulated.

Figure 2A:
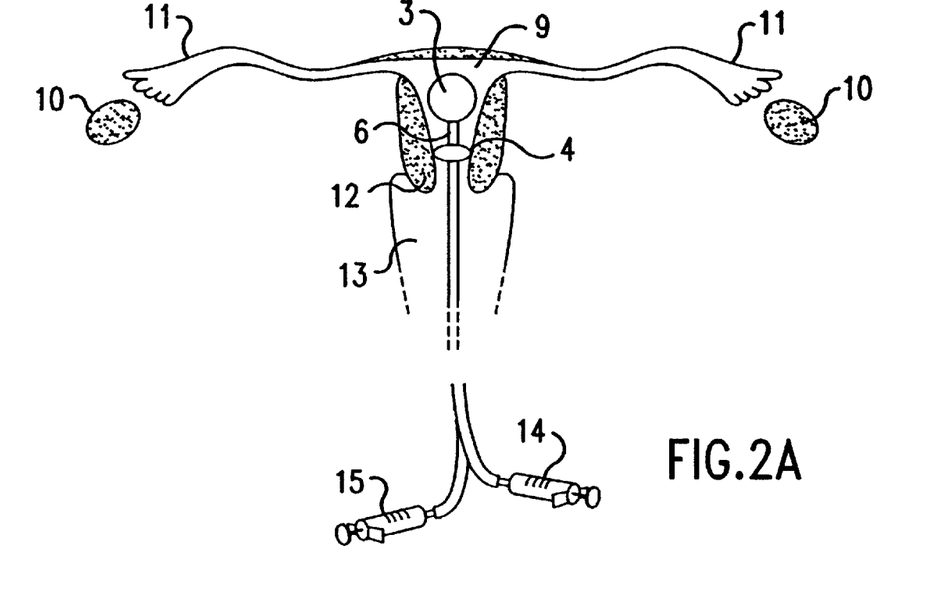
FIG. 2A shows an embodiment, where an inflatable body (3) has been introduced in the uterus, with an inflatable cuff (4) closing the cervix.

In FIG. 2A, an inflatable, NO permeable body (3) is shown positioned in the uterus (9) together with an inflatable cuff (4) closing the cervix. Further in FIG. 2, (10) denotes the ovaries, (11) the oviducts, (5) a catheter, (12) the portio vaginalis, (13) the vagina, and (14) a device, e.g., a syringe for inflating the body (3) and aspiring a sample and (15) a device, e.g., a syringe for inflating the cuff (4).

Figure 2B:
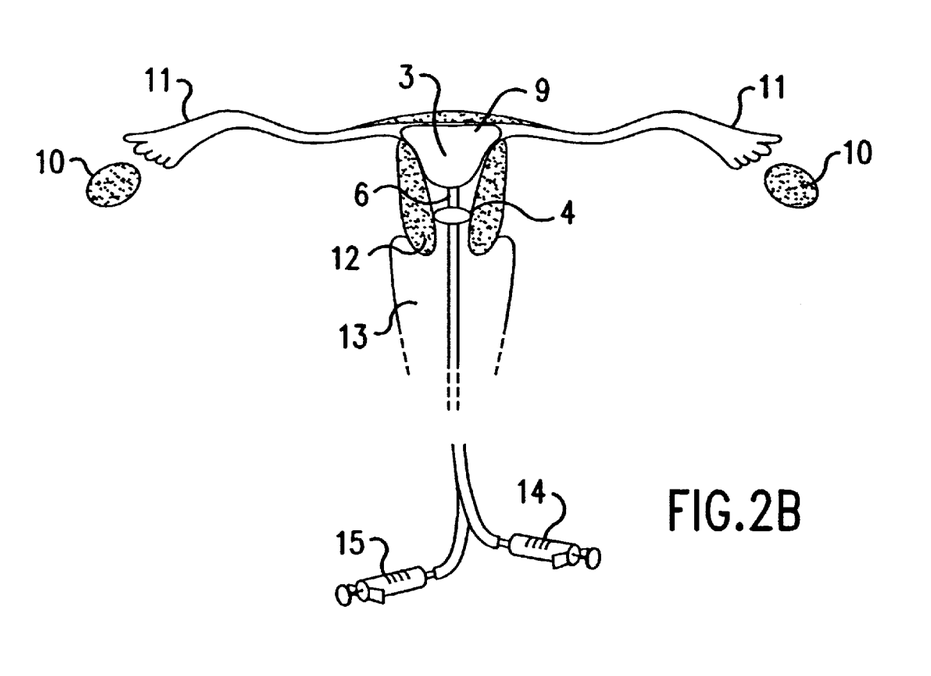
FIG. 2B shows the previous embodiment, when the inflatable body (3) has been inflated and fills the uterus, conforming to the shape of the same.

FIG. 2B shows the NO permeable body (3) in an inflated condition. According to a preferred embodiment, this body is only partially made of NO permeable material. By inserting an inflatable body, only partially permeable to NO, it becomes possible to localize the inflammatory condition to either the rigth or left ovary/oviduct. Preferably such a body, permeable to NO only on one side, can be deflated after the first sampling, turned without removing from the inner organ in question, here the uterus, and re-inflated and purged with inert gas, whereupon the sampling procedure can be repeated.

Figure 3:
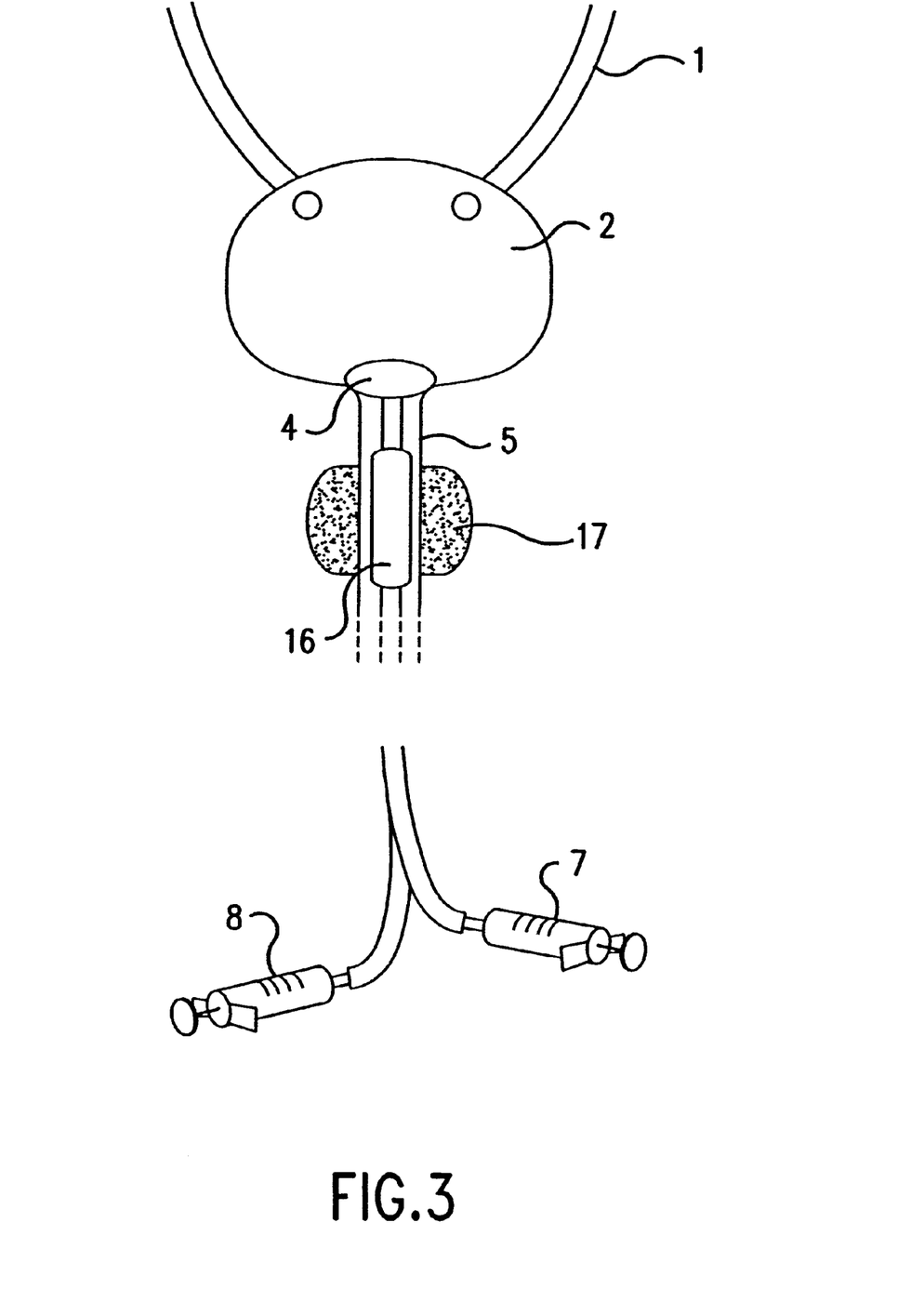
FIG. 3 shows an embodiment, where an inflatable body (16) of an anatomically adapted shape, in this case a cylinder with rounded end surfaces, has been inserted and inflated in the urethra of a male patient, positioned in the prostatic urethra. An additional inflatable body (3) in the bladder isolates the bladder from the urethra and helps in positioning the first body, FIGS. 4A, B and C show different embodiments, where the inflatable body has different anatomically adapted shapes (FIG. 4A and 4B) and as a preferred embodiment, a device allowing separate samples to be taken simultaneously in the bladder and the urethra (FIG. 4C).

In FIG. 3, an inflatable body (4) is positioned in the bladder (2) and an inflatable, NO-permeable body (16) of an anatomically adapted shape is positioned in the part of the urethra (5), surrounded by the prostate gland (17). Two devices for inflation and sampling, e.g., two syringes (7 and 8) are provided, as in FIG. 1. In FIG. 3, (1) denotes the urinary tracts, discharging into the bladder. Again, the bladder is depicted schematically, with no claims to anatomical correctness.

Figure 4A:
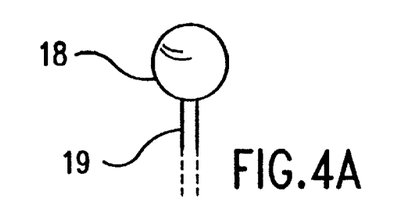
Figure 4B:
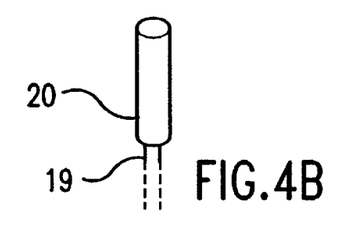
Figure 4C:
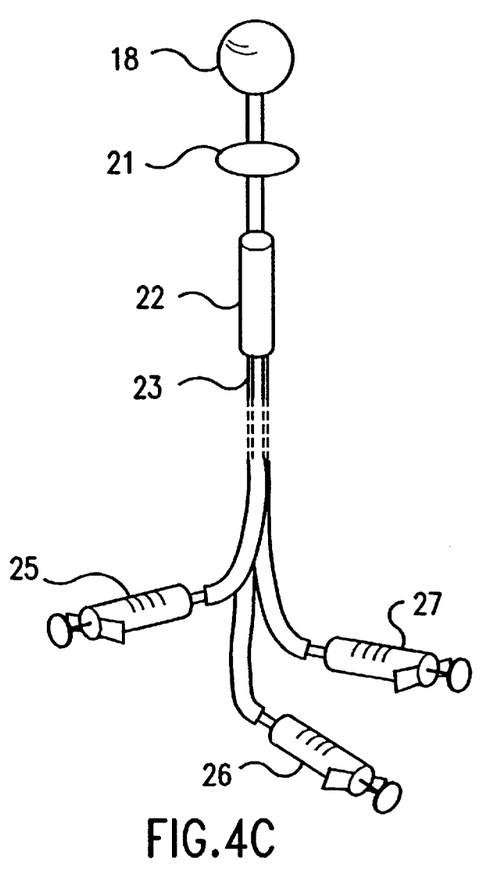

In FIG. 4A is schematically shown an example of a basic, spherical inflatable NO permeable body (18) with a catheter (19). In FIG. 4B is schematically shown an example of an inflatable NO permeable body (20) of cylindrical shape and a catheter (19). FIG. 4C schematically shows a spherical inflatable NO permeable body (18) for example insertable in the bladder, an inflatable cuff (21) for example for sealing off the bladder, an inflatable NO permeable body (22) of cylindrical shape and their catheters, collectively denoted (23). Each inflatable body is provided with its own catheter and means for inflating and aspiring, e.g., syringes (24, 25 and 26).

According to a further embodiment of the invention, briefly mentioned in connection with FIG. 2B supra, said inflatable body is only partially made of NO-permeable and liquid impermeable material in order to further enhance the possibilities of local and area specific sampling, i.e. a defined area consists of NO-permeable and liquid impermeable material, whereby the remaining area consists of material, impermeable to NO and, of course, liquid impermeable. The inflatable body could e.g. be flat and circular, whereby one side is made of NO-permeable and liquid impermeable material and the other consists of a material, impermeable to NO. Using the device, said NO-permeable area would be placed in contact with the area of interest, whereby the effect of NO, possibly present in neighbouring areas, would be minimized. To aid in the positioning of the device, the catheter is provided with a mark, coloured or other, e.g. a raised surface, a velt etc, showing the orientation of the device. It is also conceivable, that the device is provided with one or several radiopaque elements, e.g. elements showing the position and orientation of the device.

The method according to the present invention, i.e. a method for collection of endogenous gaseous nitric oxide, produced in the urinary tract epithelium, uterine or oviduct epithelium, preferably comprises local collection of endogenous gaseous nitric oxide, from a locally specific and defined inner cavity or a defined area on the epithelium on the inner or outer surface of an organ.

According to one embodiment of the invention the local production of gaseous nitric oxide is detected and quantified, and used for detection and monitoring of local inflammatory states in the urinary tract, the uterus and/or the vagina. In addition to said organs, the method and device finds utility also for determinations performed in the abdominal cavity and optionally also in other body cavities and hollow organs by mearly aapting the shape and size of the device.

According to an embodiment of the present invention, the method includes the use of a device according to the present invention, or the following steps a) an inflatable body of NO-permeable material, connected to a tube for inflation and sampling, is inserted adjacent to the organ or tissue to be studied, b) said inflatable body is inflated with a non-reactive gas or gas mixture of known composition, c) said gas or gas mixture is allowed to stand in said, NO-permeable body until equilibrium conditions are reached, whereupon d) said gas is aspirated and analyzed, e) the found concentration of NO is compared to the level for healthy individuals or with a level obtained at another occasion for the same individual.

An alternative embodiment, omitting the use of a device according to the invention, includes the following steps:

a) a non-reactive gas or gas mixture of known composition is injected in the cavity to be studied, e.g. in the urinary bladder, vagina or uterus, b) said gas or gas mixture is allowed to stand in said cavity, c) said gas or gas mixture is aspired and analyzed, d) the found concentration of NO is compared to the level for healthy individuals or with a level obtained at another occasion for the same individual.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

EXAMPLE

NO excretionw as measured in the urinary bladder in healthy controls and patients with interstitial cystitis of different etiology. The study encompassed 6 patients (age 72±4 years, 5 males) with lower urinary tract infection (lane A in FIG. 5) confirmed by urinary cultures (>10⁵ bacteria/ml), 5 female patients (age 70±5) with interstitial cystitis (lane B), diagnosed according to symptom evaluation, cystoscopy findings and bladder biopsies, 5 patients (age 71±4 years, 4 males) with cystitis due to irradiation therapy (lane C) where the urinary bladder had been in the field of irradiation (full dose 64 Gy, more than one year prior to NO measurements), and 5 patients (age 74±2 years, 3 males) with chemically induced cystitis (lane D) due to anti-tumour treatment with Bacillus Calmette-Guérin (BCG). Instillation (1 h) of BCG into the bladder had been performed once monthly for more than 6 months in all patients. Urinary tests with respect to nitrite were al negative in the 3 latter patient groups and no signs of infection could be found in these patients using reagent strip urine analysis. Controls (lane E) (n=9, age 74±4 years, 5 males) were patients undergoing routine cystoscopy during remission of bladder tumour. Only patients free from recurrent cancer as determined by cystoscopy and bladder washout cytology were included in the study.

NO-free air (100 ml, NO <5 parts per billion, ppb) was introduced into the bladder during cystoscopy. After 5 minutes of incubation, the air as aspirated into a syringe and immediately injected into a chemiluminescence NO analyzer (CLD 700, Eco Physics, Durnten, Switzerland) and peak levels of NO were registered. The detection limit for NO was 1 ppb and the analyzer was calibrated at known compositions of NO in $N_2$ using an electromagnetic flow controller (Envionics Inc., Middletown, Conn., USA). The chemiluminescence assay is highly specific for NO and there is no interference from other nitrogen oxides. NO values remained stable in the syringe for at least 2 min at widely varied concentrations (5–25,000 ppb) of NO in air.

Figure 5:
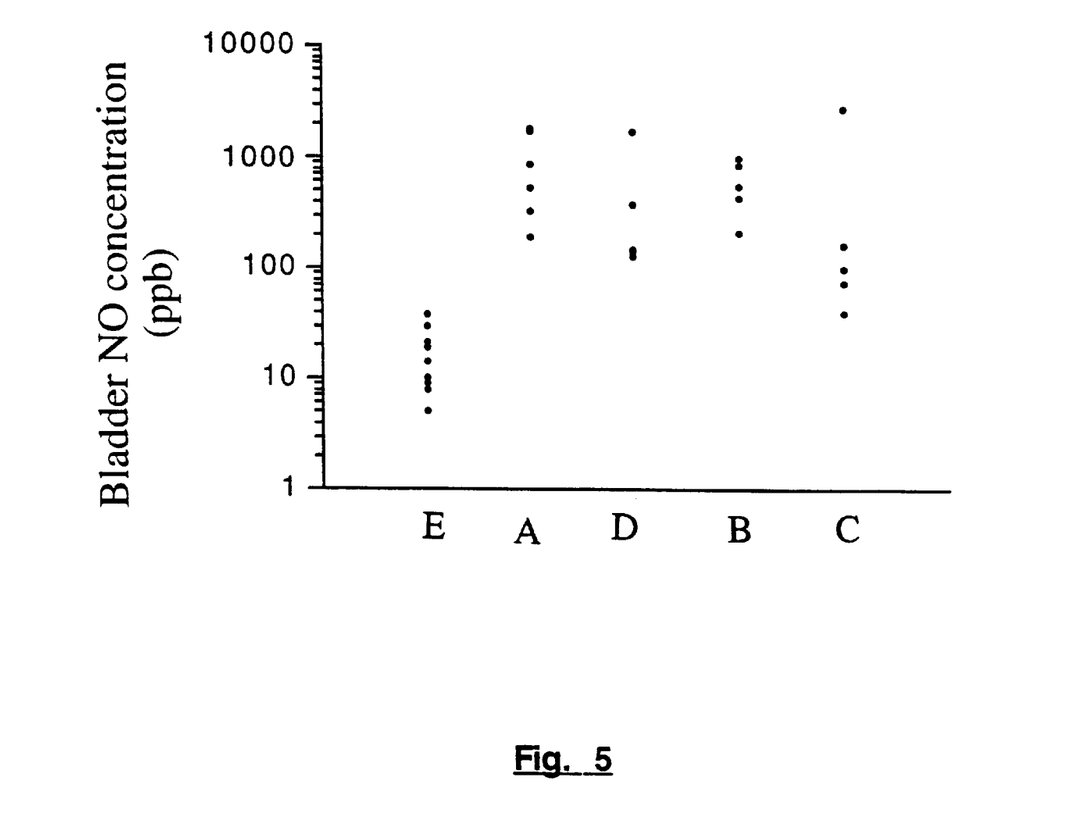
FIG. 5 shows the correlation between bladder NO concentration and the occurrence of cystitis of different etiology, compared to healthy controls.

Urinary bladder NO levels were 30–50 times higher in all varieties of cystitis compared to controls (FIG. 5). Mean (±SEM) NO concentrations were 896±282 ppb in patients with lower urinary tract infection, 616±146 ppb in interstitial cystitis, 633±540 ppb in irradiation cystitis, and 510±313 ppb in the BCG treated patients. In controls, mean NO values were 17±3 ppb (p<0.001 compared to all groups of patients, Mann-Whitney U test). The results show, that bladder NO measurements are useful in the diagnosis and monitoring of cystitis, regardless of etiology.

Separate animal studies (conducted in pigs) and studies in vitro, have shown that, using an inflatable body of NO-permeable but liquid impermeable material, sampling times of about 10 minutes may be sufficient. Within this time the concentration of NO in the inflatable body equilibrates with the surrounding concentration.

What is claimed is:

1. Device for localized collection of endogenous gaseous nitric oxide, characterized in that said device includes at least one inflatable body made of NO permeable and liquid impermeable material, at least one tube for inflation and sampling and means for inflating said body or bodies with a non reactive gas or gas mixture of known composition and aspiring and analysing the gas mixture or mixtures aspired.

2. Device according to claim 1, characterized in that the inflatable body of NO permeable and liquid impermeable material has a three-dimensional shape, adapted to specific organs and defined areas in specific organs.

3. Device according to claim 1, characterized in that said inflatable body of NO permeable and liquid impermeable material has one of the following shapes; cylindrical with rounded end surfaces, spherical, semi-spherical, conical, ellipsoid, pear-shaped or a flattened sphere or flattened ellipsoid.

4. Device according to any one of the previous claims, characterized in that said device comprises one or several inflatable bodies for anatomically positioning said device and sealing off neighbouring body cavities during sampling.

5. Device according to any one of claim 2–3, characterized in that said inflatable body consists of a defined area of NO permeable and liquid impermeable material, whereby the remaining area consists of material, impermeable to NO and to liquids.

6. Device according to claim 1, characterized in that the NO permeable and liquid impermeable material is chosen from the group, comprising silicon, chloroprene rubber and cation exchange materials.

7. Device according to claim 1, characterized in that said device is adapted for use in connection with an urethroscope, vaginoscope, hysteroscope or similar instrument.

8. Method for collection of endogenous gaseous nitric oxide, produced in or on the surface of an urogenital organ, for example the urinary tract epithelium or the uterine or oviduct epithelium, characterized in that the endogenous gaseous nitric oxide is collected locally, from a defined inner cavity or a defined area on the epithelium on the inner or outer surface of such organ.

9. Method according to claim 8, characterized in that a) a non-reactive gas or gas mixture of known composition is introduced in the urogenital cavity to be studied, e.g. in the urinary bladder, uterus or oviducts, b) said gas or gas mixture is allowed to stand in said cavity, c) said gas or gas mixture is aspired and analyzed.

10. Method according to claim 8, characterized in that a) at least one inflatable body of NO-permeable and liquid impermeable material, connected to a tube for inflation and sampling, is inserted in an organ adjacent to the tissue to be studied, b) said inflatable body or bodies is/are inflated with a non-reactive gas or gas mixture of known composition, c) said gas or gas mixture or mixtures is/are allowed to stand in said, NO permeable body until equilibrium conditions are reached, whereupon d) said gas/gases is/are aspired and analyzed.

11. Method in the diagnosis of inflammatory conditions in the urogenital organs, characterized in that NO is measured in gas sampled from said organs and a found level being compared to the level for healthy individuals or with the level obtained at another occasion for the same individual.

12. Method in the diagnosis of inflammatory conditions in the urinary organs, preferably the bladder and urinary tract, characterized in that NO is measured in gas sampled from said organs and a found level being compared to the level for healthy individuals or with the level obtained at another occasion for the same individual.

13. Method according to claim 12, characterized in that an increased level is taken as an indication of any one of the following conditions; interstitial cystitis, irradiation cystitis, chemically induced cystitis, prostatitis.

14. Method in the diagnosis of inflammatory conditions in the genital organs, preferably the uterus and oviducts, characterized in that NO is measured in gas sampled from said organs and a found level being compared to the level for healthy individuals or with the level obtained at another occasion for the same individual.

15. Method according to claim 13, characterized in that an increased level is taken as an indication of any one of the following conditions; salpingitis, inflammation of the uterus, endometritis, endometriosis, urethritis of different genesis, extrauterine pregnancy.

16. System for use in the diagnosis of inflammatory conditions in the urogenital organs, comprising at least one body of NO permeable and liquid impermeable material, at least one fluid conduit connected to said; at least one body for inflation, sampling and purging, means for supplying a non reactive gas or gasmixture to said at least one body, means for aspiring the gas mixture in said at least one body, means for analyzing the composition of said, gas mixture, and means for displaying the results.

17. System according to claim 16, wherein the inflatable at least one body is only partially NO permeable and the system comprises means for positioning and/or indicating the position and orientation of said at least one body.

* * * * *